(12) United States Patent
Hareland (10) Patent No.: US 9,861,422 B2
(45) Date of Patent: Jan. 9, 2018

(54) CATHETER BREACH LOOP FEEDBACK FAULT DETECTION WITH ACTIVE AND INACTIVE DRIVER SYSTEM

(71) Applicant: Medtronic, Inc., Minneapolis, MN (US)

(72) Inventor: Scott A Hareland, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 195 days.

(21) Appl. No.: 14/741,637

(22) Filed: Jun. 17, 2015

(65) Prior Publication Data
US 2016/0367305 A1    Dec. 22, 2016

(51) Int. Cl.
*A61B 18/02* (2006.01)
*G01M 3/40* (2006.01)
(Continued)

(52) U.S. Cl.
CPC .......... *A61B 18/02* (2013.01); *A61B 18/1233* (2013.01); *G01M 3/40* (2013.01);
(Continued)

(58) Field of Classification Search
None
See application file for complete search history.

(56) References Cited

U.S. PATENT DOCUMENTS 4,363,556 A    12/1982 Belliveau et al.
5,015,996 A *  5/1991 Konishi ............... H01H 47/002
                                          200/61.05
(Continued)

FOREIGN PATENT DOCUMENTS

EP    1980287 A2    10/2008
EP    2218418 A2     8/2010
(Continued)

OTHER PUBLICATIONS

International Search Report and Written Opinion dated Sep. 21, 2016, for corresponding International Application No. PCT/US2016/036614; International Filing Date: Jun. 9, 2016 consisting of 12-pages.

*Primary Examiner* — Jermele M Hollington
*Assistant Examiner* — Suresh K Rajaputra
(74) *Attorney, Agent, or Firm* — Christopher & Weisberg, P.A.

(57) ABSTRACT

A fault-detection method, system, and device for a cryosurgical system that avoids a false-positive detection of a fault condition, such as fluid ingress within the system. The fault-detection mechanism may generally include a driver having an active mode and an inactive mode, the driver generating an output signal when the driver is in active mode, a detector, the detector capable of receiving the driver output signal, and a detector verification controller in communication with the driver and the detector, the detector verification controller changing the driver from the active mode to the inactive mode when the detector receives the driver output signal. The controller may determine a true fault condition if the controller determines there is a correlation between the signal received by the detector and the driver output signal. All other possible fault conditions may be ignored if the controller determines that the signals are not correlated.

18 Claims, 5 Drawing Sheets

(51) Int. Cl.
 *A61B 18/12* (2006.01)
 *A61B 18/00* (2006.01)
(52) U.S. Cl.
 CPC .............. *A61B 2018/0066* (2013.01); *A61B 2018/00642* (2013.01); *A61B 2018/00779* (2013.01); *A61B 2018/00827* (2013.01); *A61B 2018/00898* (2013.01); *A61B 2018/0212* (2013.01); *A61B 2018/0262* (2013.01)

(56) References Cited

U.S. PATENT DOCUMENTS

| | | | |
|---|---|---|---|
| 6,298,255 B1* | 10/2001 | Cordero | A61B 5/04085 600/372 |
| 6,383,180 B1 | 5/2002 | Lalonde et al. | |
| 6,468,268 B1* | 10/2002 | Abboud | A61B 18/02 606/20 |
| 6,569,158 B1 | 5/2003 | Abboud et al. | |
| 6,682,525 B2 | 1/2004 | Lalonde et al. | |
| 6,733,494 B2 | 5/2004 | Abboud et al. | |
| 6,761,714 B2 | 7/2004 | Abboud et al. | |
| 6,887,234 B2 | 5/2005 | Abboud et al. | |
| 7,004,936 B2 | 2/2006 | Ryba et al. | |
| 7,303,554 B2 | 12/2007 | Lalonde et al. | |
| 7,404,816 B2 | 7/2008 | Abboud et al. | |
| 7,442,190 B2 | 10/2008 | Abbound et al. | |
| 7,527,622 B2 | 5/2009 | Lane et al. | |
| RE40,868 E | 8/2009 | Ryba et al. | |
| 7,716,966 B2 | 5/2010 | Abboud et al. | |
| 7,727,191 B2 | 6/2010 | Mihalik et al. | |
| 7,727,228 B2 | 6/2010 | Abboud et al. | |
| 7,842,031 B2 | 11/2010 | Abboud et al. | |
| 7,905,879 B2 | 3/2011 | Abboud et al. | |
| 7,914,525 B2 | 3/2011 | Abboud et al. | |
| 7,956,620 B2* | 6/2011 | Gilbert | A61B 18/1233 324/649 |
| 8,206,345 B2 | 6/2012 | Abboud et al. | |
| 8,225,643 B2 | 7/2012 | Abboud et al. | |
| 8,297,108 B2 | 10/2012 | Abboud et al. | |
| 8,298,217 B2 | 10/2012 | Lane et al. | |
| 8,382,747 B2 | 2/2013 | Abboud et al. | |
| 8,425,456 B2 | 4/2013 | Mihalik et al. | |
| 8,454,587 B2 | 6/2013 | Lalonde et al. | |
| 8,467,872 B2 | 6/2013 | Hareland | |
| 8,491,636 B2 | 7/2013 | Abboud et al. | |
| 8,545,491 B2 | 10/2013 | Abboud et al. | |
| 8,626,287 B2 | 1/2014 | Hareland | |
| 8,696,656 B2 | 4/2014 | Abboud et al. | |
| 8,771,264 B2 | 7/2014 | Abboud et al. | |
| 8,900,222 B2 | 12/2014 | Abboud et al. | |
| 8,965,506 B2 | 2/2015 | Hareland et al. | |
| 9,027,389 B2 | 5/2015 | Abboud et al. | |
| 9,050,069 B2 | 6/2015 | Lalonde et al. | |
| 2003/0018326 A1* | 1/2003 | Abboud | A61B 18/02 606/20 |
| 2004/0158238 A1 | 8/2004 | Lalonde et al. | |
| 2004/0243119 A1* | 12/2004 | Lane | A61B 18/02 606/21 |
| 2004/0267249 A1 | 12/2004 | Abboud et al. | |
| 2005/0215989 A1 | 9/2005 | Abboud et al. | |
| 2005/0228367 A1* | 10/2005 | Abboud | A61B 18/02 606/20 |
| 2005/0288657 A1 | 12/2005 | Lentz et al. | |
| 2006/0004350 A1 | 1/2006 | Ryba | |
| 2006/0122589 A1 | 6/2006 | Abboud et al. | |
| 2007/0032783 A1 | 2/2007 | Abboud et al. | |
| 2008/0039791 A1 | 2/2008 | Abboud et al. | |
| 2008/0077124 A1 | 3/2008 | Lalonde et al. | |
| 2008/0147135 A1 | 6/2008 | Hareland | |
| 2008/0154187 A1* | 6/2008 | Krulevitch | A61M 5/14526 604/48 |
| 2008/0200828 A1 | 8/2008 | Abboud et al. | |
| 2008/0200829 A1 | 8/2008 | Abboud et al. | |
| 2008/0221508 A1 | 9/2008 | Abboud et al. | |
| 2009/0030288 A1 | 1/2009 | Abboud et al. | |
| 2009/0088735 A1 | 4/2009 | Abboud et al. | |
| 2009/0182318 A1 | 7/2009 | Abboud et al. | |
| 2009/0182319 A1 | 7/2009 | Lane et al. | |
| 2009/0201048 A1 | 8/2009 | Yao et al. | |
| 2010/0114269 A1 | 5/2010 | Wittenberger et al. | |
| 2010/0204687 A1 | 8/2010 | Abboud et al. | |
| 2010/0211056 A1 | 8/2010 | Mihalik et al. | |
| 2011/0184399 A1 | 7/2011 | Wittenberger | |
| 2012/0010554 A1* | 1/2012 | Vantard | A61M 1/16 604/6.04 |
| 2012/0035601 A1 | 2/2012 | Wittenberger | |
| 2012/0089047 A1 | 4/2012 | Ryba et al. | |
| 2012/0158012 A1 | 6/2012 | Sandhu et al. | |
| 2012/0232547 A1 | 9/2012 | Cohen | |
| 2012/0271291 A1 | 10/2012 | Abboud et al. | |
| 2012/0316070 A1 | 12/2012 | Murphy | |
| 2013/0109985 A1 | 5/2013 | Gillberg et al. | |
| 2013/0172866 A1 | 7/2013 | Abboud et al. | |
| 2013/0211394 A1 | 8/2013 | Fischer et al. | |
| 2013/0218151 A1 | 8/2013 | Mihalik et al. | |
| 2013/0336356 A1 | 12/2013 | Martin et al. | |
| 2014/0180278 A1 | 6/2014 | Abboud et al. | |
| 2014/0276712 A1 | 9/2014 | Mallin et al. | |
| 2014/0296736 A1 | 10/2014 | Abboud et al. | |
| 2014/0340796 A1 | 11/2014 | Sandhu et al. | |
| 2014/0379039 A1 | 12/2014 | Hareland et al. | |
| 2015/0045781 A1 | 2/2015 | Abboud et al. | |
| 2015/0080794 A1 | 3/2015 | Duong et al. | |
| 2015/0198501 A1* | 7/2015 | Rule | A61M 5/1413 73/40.5 R |

FOREIGN PATENT DOCUMENTS

| | | |
|---|---|---|
| EP | 2269528 A2 | 1/2011 |
| EP | 2294997 A1 | 3/2011 |
| WO | 2000042931 A1 | 7/2000 |
| WO | 2000042932 A1 | 7/2000 |
| WO | 2000042933 A1 | 7/2000 |
| WO | 2005089853 A1 | 9/2005 |
| WO | 2006017073 A2 | 2/2006 |
| WO | 2006096272 A1 | 9/2006 |
| WO | 2006119615 A1 | 11/2006 |
| WO | 2006124176 A1 | 11/2006 |
| WO | 2006124177 A1 | 11/2006 |
| WO | 2008000064 A1 | 1/2008 |
| WO | 2008000065 A1 | 1/2008 |
| WO | 2008046183 A1 | 4/2008 |
| WO | 2009137924 A1 | 11/2009 |
| WO | 2010081221 A1 | 7/2010 |
| WO | 2011050458 A1 | 5/2011 |
| WO | 2011091508 A1 | 8/2011 |
| WO | 2012016320 A1 | 2/2012 |
| WO | 2014149925 A1 | 9/2014 |

* cited by examiner

CATHETER BREACH LOOP FEEDBACK FAULT DETECTION WITH ACTIVE AND INACTIVE DRIVER SYSTEM

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a fault-detection method, system, and device for a cryosurgical system that avoids a false-positive detection of a fault condition, such as fluid ingress within the system.

BACKGROUND

Cryotreatment may be used to treat a variety of conditions, such as atrial fibrillation, tumor treatment, and others. Generally, cryotreatment involves circulating a refrigerant from a refrigerant source through one or more fluid delivery conduits and into the cryotreatment device, wherein the refrigerant expands and cools a portion of the cryotreatment device to treatment temperatures. The cryotreatment device may be in fluid communication with a vacuum source that facilitates removal of expanded refrigerant from the cryotreatment device and through one or more fluid recovery conduits.

Cryotreatment devices may develop leaks, which not only impacts cooling efficiency but also threatens patient welfare. Many devices include a leak detection mechanism at some location within a fluid pathway that can be used to detect a fault (for example, a fluid leak within the device or blood ingress) and alert the user. In some cases, fluid delivery is stopped and/or the vacuum source is inactivated to help ameliorate the condition. However, the leak detection mechanism may communicate a false positive fault condition to the user. In such a case, the procedure delay caused by the system shutdown not only extends the time required for the medical procedure, but frequent system shutdowns may cause excessive mechanical or electrical wear on the system.

Currently known fault-detection mechanisms include a driver that sends a signal along an electrical pathway in which a detector is placed at the other end of a normally open circuit. If blood or fluid enters the system, the fault-detection mechanism identifies a fault condition. However, false detection of a fault condition may be caused by external sources, such as electromagnetic interference with the detection line. Such interference is frequently encountered when using a medical device including a leak-detection mechanism is used for electrophysiology procedures, especially where certain mapping or ablation equipment is in use (for example, Carto-3 mapping systems). Although some workarounds may be available, these are inconvenient and many are not well known, especially by less-experienced users.

It is therefore desired to provide a fault-detection method, system, and device for a cryosurgical system that avoids false-positive fault detection.

SUMMARY

The present invention advantageously provides a fault-detection method, system, and device for a cryosurgical system that avoids a false-positive detection of a fault condition, such as fluid ingress within the system. A fault-detection mechanism may generally include a driver having an active mode and an inactive mode, the driver generating an output signal when the driver is in active mode, a detector, the detector capable of receiving the driver output signal, and a detector verification controller in communication with the driver and the detector, the detector verification controller changing the driver from the active mode to the inactive mode when the detector receives the driver output signal. The driver and the detector may define an electrical circuit having an open condition and a closed condition, and the detector may receive the driver output signal when the electrical circuit is in the closed condition. For example, the electrical circuit may be in the closed condition when a fluid shunts the driver output signal to the detector. Receipt of the driver output signal by the detector may indicate a possible fault condition. The detector verification controller may be programmed to determine a value of correlation between the driver output signal and the signal received by the detector. For example, the detector verification controller may determine that the possible fault condition is a true fault condition when the correlation value is above a predetermined threshold and may determine that the possible fault condition is a false-positive fault condition when the correlation value is below a predetermined threshold. As a non-limiting example, the predetermined threshold may be 80%. Further, the fault-detection mechanism may generate an alert only when the detector verification controller determines that the possible fault condition is a true fault condition and not when the detector verification controller determines that the possible fault condition is a false-positive fault condition.

A system for fluid ingress detection may generally include an electrical circuit having a closed condition and an open condition, the electrical circuit including: a driver having an active mode and an inactive mode, the driver generating an output signal when the driver is in active mode; a detector capable of receiving the output signal when the electrical circuit is in the closed condition; and a detector verification controller in communication with the driver and the detector, the detector verification controller changing the driver from the active mode to the inactive mode when the detector receives the driver input signal. Receipt of the driver output signal by the detector may indicate a possible fluid ingress condition. The detector verification controller may be programmed to determine a value of correlation between the driver output signal and the signal received by the detector. For example, the detector verification controller may determine that the fluid ingress is present when the correlation value is above a predetermined threshold and may determine that fluid ingress is not present when the correlation value is below a predetermined threshold.

A method of indentifying a fault within a medical system may include generating an output signal from an active driver in an electrical circuit, receiving the output signal by a detector, inactivating the driver, and then determining a correlation value between the output signal from the driver and the received signal by the detector. A fault condition may be indicated when the correlation value is equal to or greater than a predetermined threshold value and a no-fault condition is indicated when the correlation value is less than a predetermined threshold value. As a non-limiting example, the predetermined threshold value is 80%.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1A:
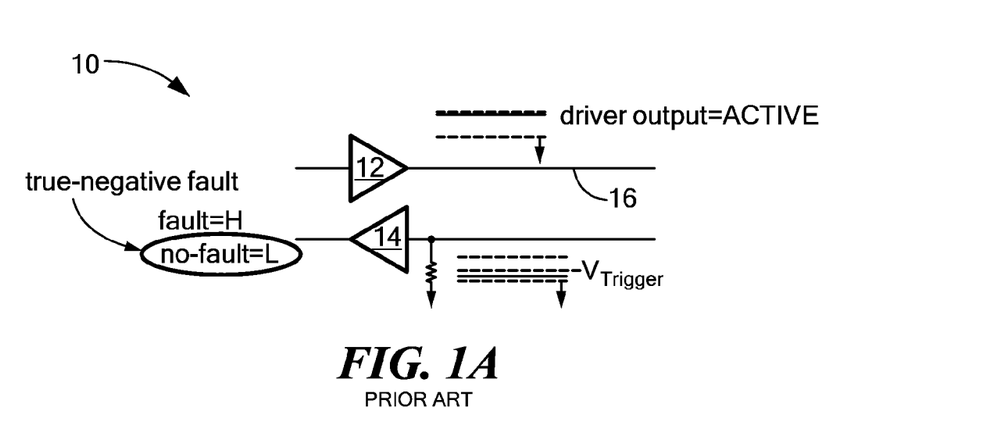
FIG. 1A shows a schematic representation of a fault-detection mechanism known in the prior art, the fault-detection mechanism identifying a true negative fault condition.
Figure 1B:
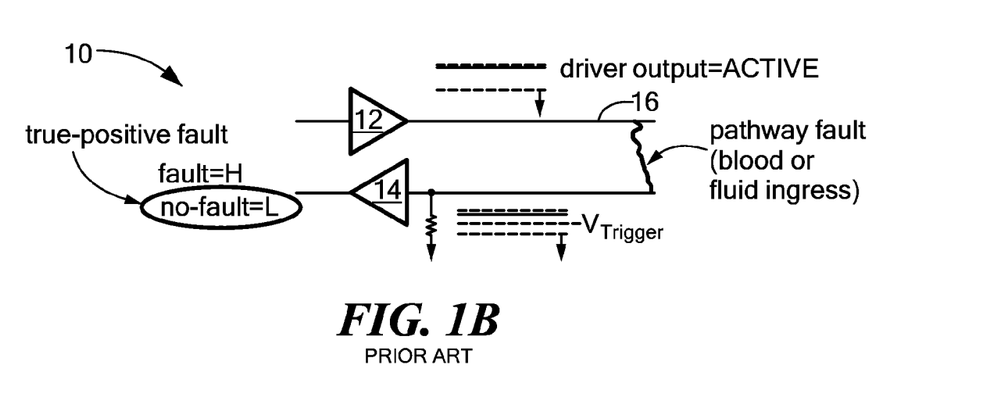
FIG. 1B shows a schematic representation of the fault-detection mechanism known in the prior art, the fault-detection mechanism identifying a true positive fault condition.
Figure 1C:
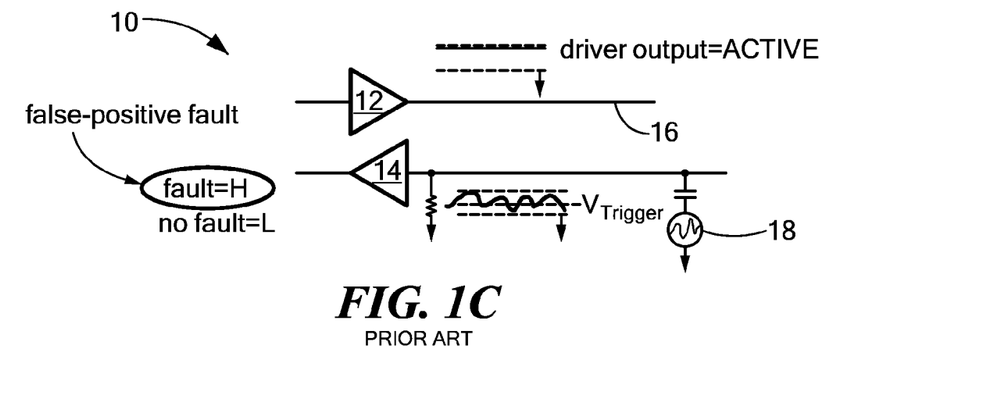
FIG. 1C shows a schematic representation of the fault-detection mechanism known in the prior art, the fault-detection mechanism identifying a false positive fault condition.

Referring now to FIGS. 1A-1C, a fault-detection mechanism known in the prior art is shown. In the currently known fault-detection mechanisms 10, such as those for the detection of blood within a fluid pathway or medical device, a driver 12 is used that sends a signal along an electrical pathway in which a detector 14 is placed at the other end of a normally open circuit to monitor for the presence of blood or fluid ingress in the system. However, false detection of fluid (that is, a false-positive indication of a fault condition) in these designs is sometimes triggered by external sources, such as electromagnetic interference with the detection line, which causes the fault-detection mechanism to identify a fault condition.

In the commonly known fault-detection mechanism 10 shown in FIGS. 1A-1C, the driver 12 and the detector 14 together define a parallel electrical circuit. The driver 12 may have an active mode and an inactive mode, and may generate an output signal 16 (for example, AC or DC) when in active mode. The detector 14 detects or monitors the presence of the active driver 12 output signal, which indicates a fault condition in the system, such as blood or fluid ingress. For example, a fluid may act as a shunt to close the usually open driver-detector circuit. In a situation in which there is no fluid ingress (as shown in FIG. 1A), the detector 14 does not detect the active driver 12 output signal, or does not detect the active driver 12 signal at a voltage that is equal to or greater than a trigger voltage, and the detector 14 therefore does not indicate a fault condition. That is, the detector 14 does not indicate a fault condition when the detector input<$V_{Trigger}$.

In a situation in which fluid has entered the system (as shown in FIG. 1B) and the normally open circuit is shunted by the fluid and closes the circuit, the detector 14 will detect the active driver 12 output signal and indicate a fault condition. That is, the detector 14 indicates a fault condition when the detector input>$V_{Trigger}$.

In a situation in which the a source of noise 18 is present on the electrical pathway, such as electromagnetic interference, the fault-detection mechanism 10 may confuse the noise with the active driver 12 output signal and indicate a false-positive fault condition (as shown in FIG. 1C). That is, the detector 14 indicates a false-positive fault condition when the detector input>$V_{Trigger}$. This situation may require user intervention, system restart, or transition to a fault-handling mode, all of which are undesired conditions when the system should be operating normally.

Figure 2:
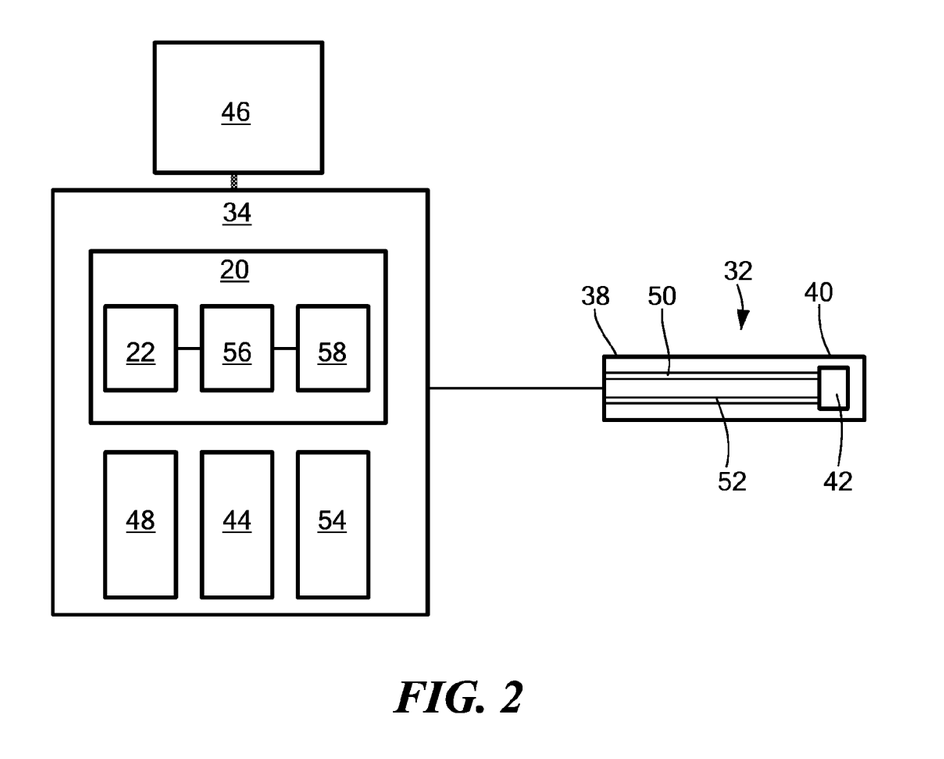
FIG. 2 shows a schematic representation of a system including a console, medical device, and a fault-detection mechanism in accordance with the present application.

Referring now to FIGS. 2-5B, a fault-detection mechanism 20 including a detector verification controller 22 is shown, and FIG. 2 shows a schematic representation of a medical system 30 including a cryotreatment device 32, a console 34, and one or more fault-detection mechanisms 20. The cryotreatment device 32 may be any device through which a fluid is circulated, such a refrigerant used for cryotreatment of tissue. As a non-limiting example, the cryotreatment device 32 may include a proximal portion 38 and a distal portion 40, with an expansion chamber 42 at or within the distal portion 40. For example, the cryotreatment device 32 may include an expandable element (not shown), such as a balloon, defining an expansion chamber 42. Additionally or alternatively, the cryotreatment device 32 may include a non-expandable distal portion 40 defining an expansion chamber 42, such as may be the case if the cryotreatment device is a cryoprobe or focal catheter. The cryotreatment device 32 may also include one or more other energy delivery elements, such as electrodes in communication with an energy source (for example, radiofrequency energy), laser diode, or the like (not shown).

The cryotreatment device 32 may be in communication with the console 34, which may generally include a refrigerant source 44, one or more computers 46, and/or one or more energy sources 48. The system 30 may also include one or more fluid conduits in the cryotreatment device and the console. For example, a fluid delivery 50 conduit may be in fluid communication with the refrigerant source 44 and the cryotreatment device 32, and may deliver refrigerant from the refrigerant source 44 to the expansion chamber 42 of the cryotreatment device 32. Further, a fluid recovery conduit 52 may be in fluid communication with the expansion chamber 42 and a vacuum source 54 to withdraw expanded refrigerant from the cryotreatment device 32.

The one or more computers 46 may be programmed to execute one or more algorithms for the receipt, processing, and/or interpretation of signals from the one or more fault-detection mechanisms 20. As discussed in more detail below, at least a part of each fault-detection mechanism 20 may be within or a component of the one or more computers 46 and capable of interpreting and communicating fault condition determinations. The results of the fault-detection mechanism signal interpretation may be communicated by the console 34 to a user through one or more displays, audio devices, light displays, alerts, or other means. Based at least in part on the communicated fault status, the user may manually adjust system settings and/or the system may automatically or semi-automatically adjust system settings. As a non-limiting example, a fault condition identified by a fault-detection mechanism and communicated by the system may prompt the user to inactivate the vacuum source and/or the delivery of refrigerant to the cryotreatment device 32. Alternatively, the system may automatically or semi-automatically perform the same tasks.

Figure 3A:
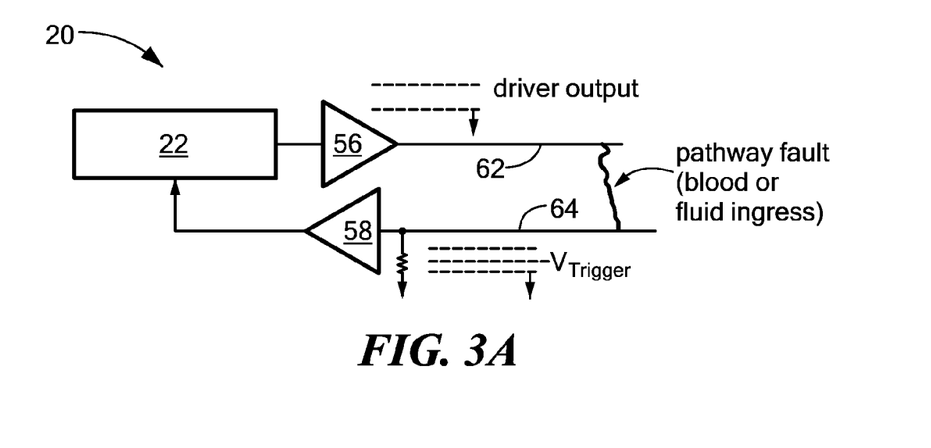
FIG. 3A shows a schematic representation of a fault-detection mechanism in accordance with the present application, the fault-detection mechanism including a detector verification controller.

Referring now to FIGS. 3A-5B, the fault-detection mechanism 20 is shown in greater detail. The fault-detection mechanism may include a driver 56 and a detector 58. Unlike commonly known fault-detection mechanisms 10 (as shown in FIGS. 1A-1C), the fault-detection mechanism 20 of FIGS. 3A-5B may also include a detector verification controller 22 that actively controls the driver 56 (as shown in FIG. 3A). The one or more fault-detection mechanisms 20, which may be located in the cryotreatment device 32, in one or more fluid conduits, and/or the console 34. As a non-limiting example, a fault-detection mechanism 20 may be located within the console 34, even though the fault-detection mechanism may detect a fault (such as a leak or blood ingress) within the cryotreatment device 32. Further, at least the detector verification controller 22 may be within or a component of the one or more computers 46 of the console 34. However, it will be understood that the fault-detection mechanism 20 or components thereof may be located anywhere in the system 30 that allows for the detection of a system fault such as fluid ingress.

Similar to the fault-detection mechanism 10 shown and described in FIGS. 1A-1C, the driver 56 and the detector 58 may together define a parallel electrical circuit that has an open condition (such as when no fault is present) and a closed condition (such as when fluid ingress is present). The driver 56 may have an active mode and an inactive mode, and may generate an output signal 62 (for example, AC or DC) when in active mode. The detector 58 may detect or monitor the presence of the active driver output signal 62, which may indicate a fault condition in the system 30, such as blood or fluid ingress. For example, a fluid may act as a shunt to close the usually open driver-detector circuit.

The detector verification controller 22 may be hardware-based or software-based. For example, the detector verification controller 22 may be implemented as a specialized circuit in the hardware of the system 30, or it may be handled with a configurable algorithm, such as one implemented in system software.

If the detector 58 identifies a fault condition, the detector verification controller 22 may change the state of the driver 56 from "active" to "inactive," and then may continue to monitor the detector 58 for a period of time. If the state of the detector 58 responds to the driver 56 change of state, then the presence of blood or fluid in the cryotreatment device 32 is more likely. If, on the other hand, the detector 58 does not respond to the driver 56 state of change, it may be likely that the identified fault condition is due to false signals 66 in the system 30, such as electromagnetic noise or other noise sources. In such a case, the detector verification controller 22 may prevent the system 30 from communicating a false positive to the user and/or may prevent the fault-detection mechanism 20 from communicating a false positive to the system 30.

Figure 3B:
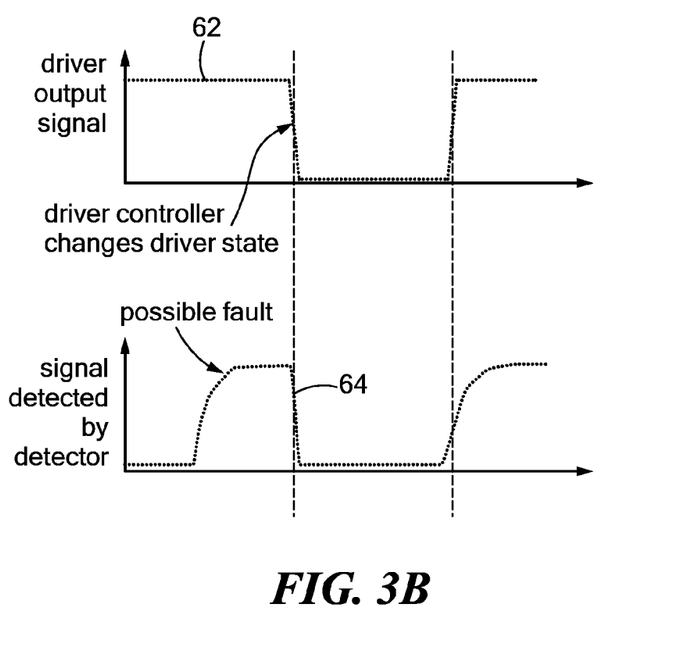
FIG. 3B shows a graphical representation of correlation between a driver output signal and a signal received by the detector of the fault-detection mechanism of FIG. 3A.

As is shown graphically in the comparison of FIG. 3B, the detector verification controller 22 may respond to the detection of a potential fault signal from the detector 58. While the detector 58 is in a no-fault state (that is, the electrical circuit is open and no fault condition is indicated), the driver/detector circuit may remain active in order to detect any fluid within the system 30 that would indicate a fault condition. This period of time may be referred to as the "initial sampling interval." If the detector 58 identifies a potential fault condition based on the driver 56 signal (for example, the detector input>$V_{Trigger}$), the detector verification controller 22 may then change the state of the driver 56 from "active" to "inactive" (or from "high" to "low," or from "on" to "off"). The detector verification controller 22 may continue to monitor the detector 58 for a period of time, which may be referred to as a "subsequent sampling interval." The detector verification controller 22 may determine or calculate a correlation between the driver output signal 62 and the signal received/detected by the detector 64 when the driver 56 is in the active and inactive modes. If the state of the detector 58 responds to the driver 56 change of state (for example, as shown in FIG. 3B), then the presence of blood or fluid in the cryotreatment device may be more likely. That is, a true fault condition may be indicated if both of the following are true:

$$(\text{input(detector)} \geq V_{Trigger} \text{ when output(driver)=ACTIVE}) \quad (1)$$

$$(\text{input(detector)} \leq V_{Trigger} \text{ when output(driver)=INACTIVE}) \quad (2)$$

The trigger voltage ($V_{Trigger}$) may be set by the user, depending on, for example, individual patient history, system design, or other factors. As a non-limiting example, the $V_{Trigger}$ may be set at approximately 30 mV (±10 mV). However, it will be understood that other trigger voltages may be used. Further, the trigger voltage may be set at a higher voltage when the state of the driver 56 is "active" than when the state of the driver 56 is "inactive." That is, $V_{Trigger-ACTIVE}$ may be greater than $V_{Trigger-INACTIVE}$.

As a non-limiting example, the percent correlation required for indication of a true fault condition may be at least 80%. Lack of a correlation (i.e. the driver-to-detector correlation is 0 or approximately 0, or is less than a predetermined threshold, such as an 80% correlation) may be used as a discriminator between true- and false-positive identifications from the detector 58. As is shown in FIG. 3B, a reduction in the driver 56 output signal 62 when the driver 56 is in the inactive mode may produce a corresponding reduction in the signal 64 received by the detector 58 when the output driver signal 62 and signal 64 received by the detector 58 are correlated.

Figure 4A:
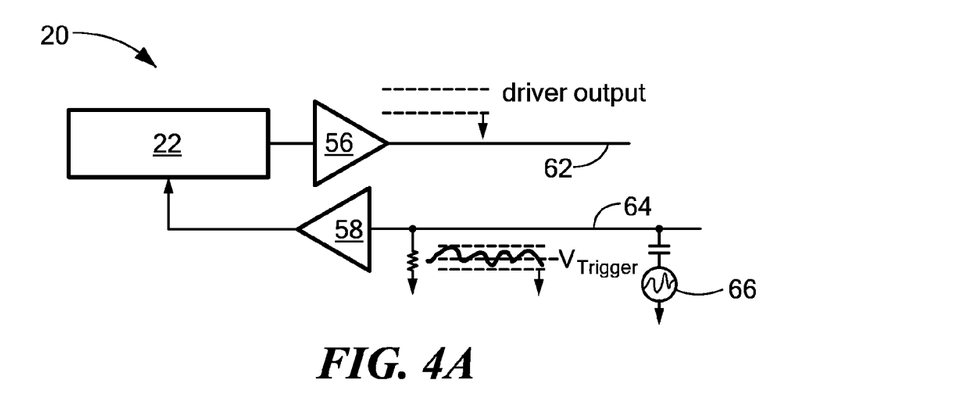
FIG. 4A shows a schematic representation of a fault-detection mechanism in accordance with the present application in the presence of a noise source, the fault-detection mechanism including a detector verification controller.
Figure 4B:
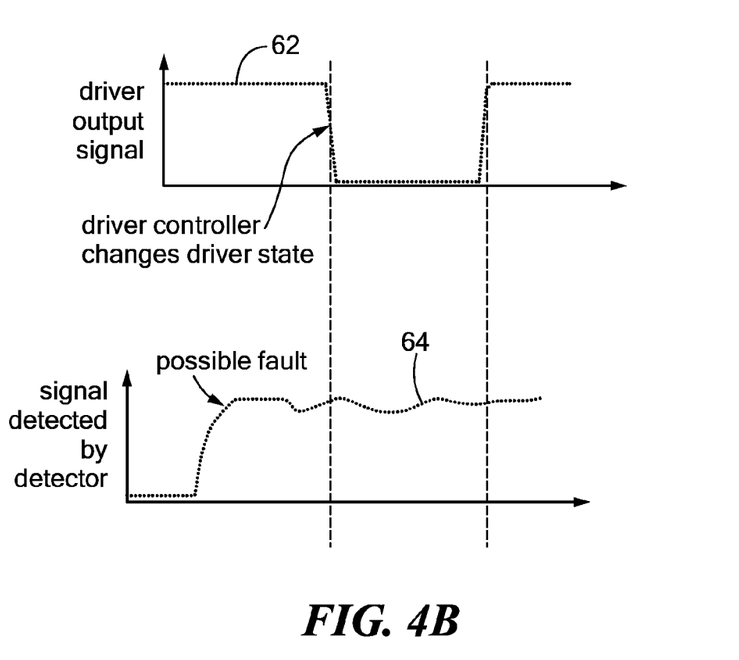
FIG. 4B shows a graphical representation of correlation between a driver output signal and a signal received by the detector of the fault-detection mechanism of FIG. 4A.

As shown in FIGS. 4A and 4B, if the detector 58 does not respond to the driver 56 change of state over the subsequent sampling interval, then it may be more likely that the detector 58 was corrupted by environmental electromagnetic interference or by other non-physical reasons. As is discussed above, while the detector 58 is in a no-fault state, the driver/detector circuit may remain active during the initial sampling interval in order to detect any fluid within the system 30 that would indicate a fault condition. If the detector 58 identifies a potential fault condition based on the driver signal 62 (for example, the detector input>$V_{Trigger}$), the detector verification controller 22 may then change the state of the driver 56 from "active" to "inactive" (or from "high" to "low," or from "on" to "off"). The detector verification controller 22 may continue to monitor the detector 58 for a subsequent sampling interval. If the state of the detector 58 does not respond to the driver 56 change of state (for example, as shown in FIG. 4B), then the presence of noise or interference with the detector may be more likely. That is, a false-positive fault condition may be avoided (that is, a true fault condition is not present) if both of the following are true:

$$\text{(input(detector)} \geq V_{Trigger} \text{ when output(driver)=ACTIVE)} \quad (3)$$

$$\text{(input(detector)} \geq V_{Trigger} \text{ when output(driver)=INACTIVE)} \quad (4)$$

As is shown in FIG. 4B, a reduction in the driver output signal 62 when the driver 56 is in the inactive mode may not produce a corresponding reduction in the signal 64 received by the detector 58 when the output driver signal and signal received by the detector 58 are not correlated.

Figure 5A:
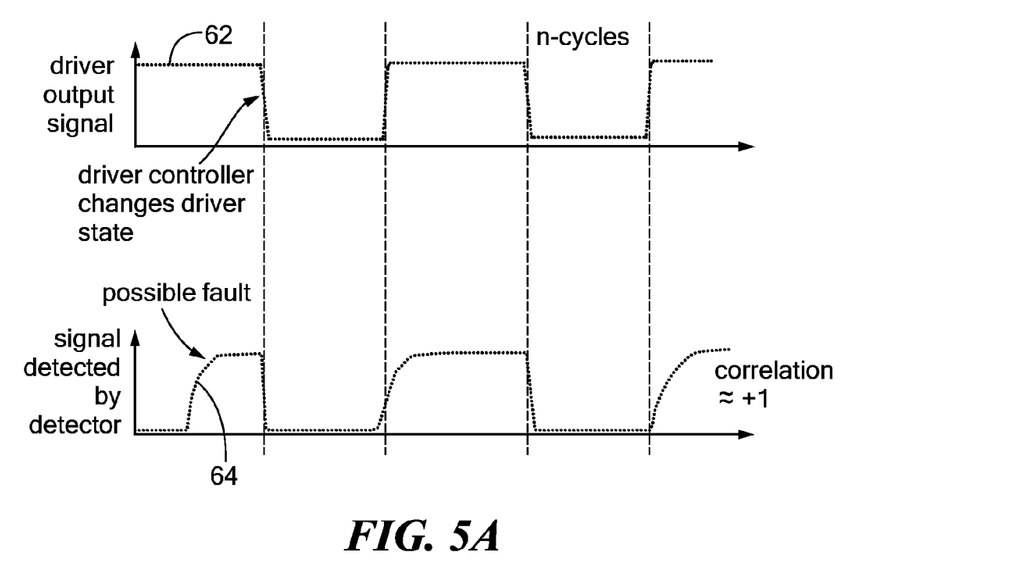
FIG. 5A shows a graphical representation of a driver output signal in a multi-cycle verification method and a graphical representation of a driver output signal in the multi-cycle verification method conducted by the fault-detection mechanism of the present application, the fault-detection mechanism identifying a false true fault condition.
Figure 5B:
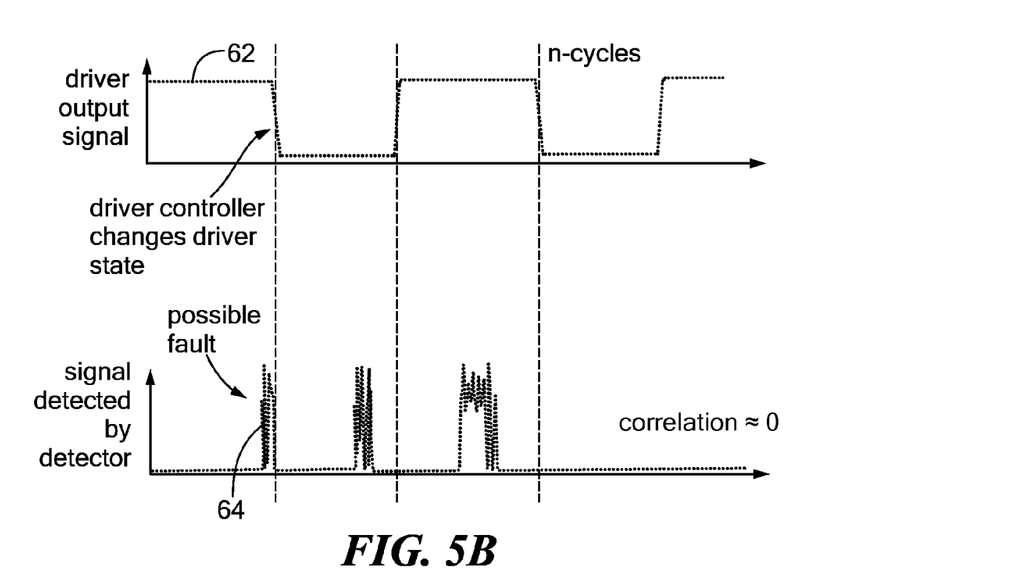
FIG. 5B shows a graphical representation of a driver output signal in a multi-cycle verification method and a graphical representation of a driver output signal in the multi-cycle verification method conducted by the fault-detection mechanism of the present application, the fault-detection mechanism avoiding the identification of a false-positive condition in the presence of a noise source.

As is shown in FIGS. 5A and 5B, the detector verification controller 22 may change the state of the driver 56 one or more times and continue to monitor the detector in order to make a final determination of the actual fault status, and the detector verification controller 22 may further be programmed to calculate or determine a correlation between the driver output signal 62 state and the signal 64 detected or received by the detector 58. That is, the fault-detection scheme may be designed to change the driver state multiple times, for n-cycles, over a plurality of sampling intervals in order to ensure that the input to the detector is consistent (i.e. that the driver-to-detector correlation is 1 or approximately 1) before identifying a fault condition. This may be beneficial in the case of transient noise interfering with the fault-detection mechanism. As a non-limiting example, the percent correlation required for indication of a true fault condition may be at least 80%. Lack of a correlation (i.e. the driver-to-detector correlation is 0 or approximately 0, or is less than a predetermined threshold, such as an 80% correlation) may be used as a discriminator between true- and false-positive identifications from the detector. For example, in the multi-cycle driver output scheme shown in FIG. 5A, a correlation of 1 or approximately 1 (shown in FIG. 5B) may indicate a true fault condition. Conversely, a correlation of 0 or approximately 0 may indicate a false fault condition caused by another mechanism, such as electromagnetic interference or noise) that should be ignored by the fault-detection mechanism.

Different driver outputs, such as AC signals of various frequencies or duty cycles, may also be used to determine if the detector is responding to the driver or to some other signal impinging on the system. As a non-limiting example, the driver output signal 62 may be at least one of sinusoid wave, square wave, sine pulses, or any other output signal waveform, as long as the detector 58 can differentiate between a received signal corresponding to an active signal (that is, a signal generated by the driver 56 in an "active" state) and a received signal corresponding to an inactive signal (that is, a signal generated by the driver 56 in an "inactive" state).

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:
1. A fault-detection mechanism comprising:
a driver having an active mode and an inactive mode, the driver being configured to generate an output signal when the driver is in active mode;
a detector, the detector configured to receive the driver output signal in a potential fault condition; and
a detector verification controller in communication with the driver and the detector, the detector verification controller being configured to:
change the driver from the active mode to the inactive mode when the detector receives the driver output signal;
monitor the detector for a subsequent sampling interval after the detector verification controller changes the driver from the active mode to the inactive mode; and
signal a true fault condition when the detector responds to the change of the driver from the active mode to the inactive mode during the subsequent sampling interval.

2. The fault-detection mechanism of claim 1, wherein the driver and the detector define an electrical circuit having an open condition and a closed condition.

3. The fault-detection mechanism of claim 2, wherein the detector receives the driver output signal when the electrical circuit is in the closed condition.

4. The fault-detection mechanism of claim 3, wherein the electrical circuit is in the closed condition when a fluid shunts the driver output signal to the detector.

5. The fault-detection mechanism of claim 3, wherein receipt of the driver output signal by the detector indicates a possible fault condition.

6. The fault-detection mechanism of claim 5, wherein the detector verification controller is programmed to determine a value of correlation between the driver output signal and the signal received by the detector.

7. The fault-detection mechanism of claim 6, wherein the detector verification controller determines that the possible fault condition is a true fault condition when the correlation value is above a predetermined threshold.

8. The fault-detection mechanism of claim 7, wherein the predetermined threshold is 80%.

9. The fault-detection mechanism of claim 6, wherein the detector verification controller determines that the possible fault condition is a false-positive fault condition when the correlation value is below a predetermined threshold.

10. The fault-detection mechanism of claim 9, wherein the predetermined threshold is 80%.

11. The fault-detection mechanism of claim 9, wherein the fault-detection mechanism does not generate an alert when the detector verification controller determines that the possible fault condition is a false-positive fault condition.

12. A system for fluid ingress detection, the system comprising:
an electrical circuit having a closed condition and an open condition, the electrical circuit including:
a driver having an active mode and an inactive mode, the driver generating an output signal when the driver is in active mode;

a detector configured to receive the output signal when the electrical circuit is in the closed condition; and a detector verification controller in communication with the driver and the detector, the detector verification controller configured to:

change the driver from the active mode to the inactive mode when the detector receives the driver input signal;

monitor the detector for a subsequent sampling interval after the detector verification controller changes the driver from the active mode to the inactive mode; and signal a fault condition when the detector responds to the change of the driver from the active mode to the inactive mode during the subsequent sampling interval.

13. The system of claim 12, wherein receipt of the driver output signal by the detector indicates a possible fluid ingress condition.

14. The system of claim 13, wherein the detector verification controller is programmed to determine a value of correlation between the driver output signal and the signal received by the detector.

15. The system of claim 14, wherein the detector verification controller determines that the fluid ingress is present when the correlation value is above a predetermined threshold.

16. The system of claim 14, wherein the detector verification controller determines that fluid ingress is not present when the correlation value is below a predetermined threshold.

17. A method of identifying a fault within a medical system, the method comprising:

generating an output signal from an active driver in an electrical circuit;

receiving the output signal by a detector;

inactivating the driver;

then, during a subsequent sampling interval after inactivating the driver, determining a correlation value between the output signal from the driver and the received signal by the detector; and then one of indicating a true fault condition when the correlation value is one of equal to and greater than a predetermined threshold value and indicating a no-fault condition when the correlation value is less than the predetermined threshold value.

18. The method of claim 17, wherein the predetermined threshold value is 80%.

* * * * *